US00PP08407P

United States Patent [19]

Guillen

[11] Patent Number: Plant 8,407

[45] Date of Patent: Oct. 5, 1993

[54] IMPATIENS PLANT 'CELEBRATION CHERRY STAR'

[75] Inventor: Mario A. Guillen, Cartago, Costa Rica

[73] Assignee: Ball Seed Co., West Chicago, Ill.

[21] Appl. No.: 824,776

[22] Filed: Jan. 23, 1992

[51] Int. Cl.[5] ..... A01H 5/00

[52] U.S. Cl. ..... Plt./87.6

[58] Field of Search ..... Plt./87.6

*Primary Examiner*—James R. Feyrer

*Attorney, Agent, or Firm*—Foley & Lardner

[57] ABSTRACT

A distinct cultivar of Impatiens plant named Celebration Cherry Star, characterized by its large, generally flat, bicolored red-pink flowers which are held above the foliage to provide a uniform display; uniform, compact, and spreading habit, dark green, non-variegated phase, and its floriferous habit.

1 Drawing Sheet

The present invention relates to a new and distinctive cultivar of Impatiens plant, botanically known as Impatiens, commercially known as New Guinea Impatiens, and referred to be the cultivar name Celebration Cherry Star. The new cultivar was developed by me at Linda Vista, Costa Rica through controlled breeding by crossing the cultivar identified as Linda Vista #N1752-2 as the female parent with the cultivar identified as Linda Vista #N1576-1 as the male parent.

Asexual reproduction of the new cultivar by terminal or stem cuttings taken at West Chicago, Ill. has shown that the unique features of this new Impatiens are stabilized and are reproduced true to type in successive propagations.

The following characteristics distinguish the new Impatiens from both its parent varieties and other cultivated Impatiens of this type known and used in the floriculture industry:

1. Generally flat, bicolored red-pink flowers.
2. Uniform, compact spreading habit.
3. Large flowers which are held above the foliage to provide a uniform display.
4. Very floriferous habit.5. Dark green, non-variegated foliage.

The accompanying colored photographs illustrate the overall appearance and flower color of the new cultivar, showing the colors as true as it is reasonably possible to obtain in colored reproductions of this type. The photograph at the top of the sheet comprises a top perspective view of a typical potted plant of Celebration Cherry Star. The photo at the bottom is a comparison view showing the flower color of Celebration Cherry Star (center), and the flowers of Sundazzle (on left) and Vulcain (on right). In the comparison photo, the depicted colors are not precise, but the different star patterns are clearly visible.

The new cultivar can be compared in certain characteristics to the cultivars Vulcain, disclosed in U.S. Plant Pat. No. 7,570, and Sundazzle, disclosed in U.S. Plant Pat. No. 6,307. A comparison of the principal characteristics of those varieties with Celebration Cherry Star appears in Chart A attached hereto. The numbers and values appearing in Chart A are based on examination of six plants for each variety, with standard deviation.

In general comparison to Vulcain, Celebration Cherry Star has:

1. A more uniform and compact habit, but also more spreading making Celebration Cherry Star a better variety for hanging baskets.
2. Larger flowers that are held above foliage in an uniform display.
3. More freely flowering habit.
4. Foliage color that is solid and not variegated like Vulcain.
5. Flowers that are flat and not cupped like flowers of Vulcain.
6. More intense flower color. (See comparison photograph.)

Compared generally to Sunshine Sundazzle, Celebration Cherry Star has:

1. A more vigorous and more spreading habit making Celebration Cherry Star a better variety for hanging baskets.
2. Larger flowers that are held above foliage in an uniform display.
3. More freely flowering habit.
4. Flowers are rounded, flat, not gappy and not cupped like flowers of Sundazzle.
5. More intense flower color. (See comparison photograph.)

The following is a detailed description of my new Impatiens cultivar based on plants produced under normal commercial practice in West Chicago, Ill., in a glass-covered greenhouse with day temperatures of 24° to 26° C. and night temperatures of 18° to 20° C.

Color references are made to the Royal Horticultural Society Colour Chart except where general terms of ordinary dictionary significance are used.

Parentage:

*Male parent.*—Linda Vista #N1576-1.

*Female parent.*—Linda Vista #N1752-2.

Propagation:

A. *Type cutting.*—Terminal tip.

B. *Time to initiate roots.*—5 days at 24° C. summer, and 7 days at 21° C. winter.

C. *Rooting habit.*—Fibrous, branching.

Plant description:

A. *Form.*—Freely branching, vigorous.

B. *Habit of growth.*—Spreading, upright habit.

C. *Foliage description.*—(1) Size: 9.5 to 11 cm in length, 4 cm in width. (2) Shape: Lanceolate, acuminate tip with attenuate base. (3) Margin: Finely serrated. (4) Color: Young foliage top side, much darker than 147A; under side, interveinal 59A. Mature foliage top side, much darker than 147A; under side, interveinal 59A. Top side color is not represented on the color chart. (5) Venation: The main vein is red-purple 59A. (6) Texture: Smooth.

D. *Internode length.*—Averages 3.5 cm.

Flowering description:

A. *Flowering habits.*—Freely flowering.

B. *Natural flowering season.*—Year-round.

C. *Flower buds.*—Conical in shape, color 50A one bud per axil.

D. *Flowers borne.*—Above foliage, arising from leaf axils on stems 148A in color.

E. *Quantity of flowers.*—Very floriferous; 8 to 10 flowers per branch are present at same time as various stages of development.

F. *Petals.*—(1) Shape: Cordate. (2) Color: Pink-red bicolor star, iridescent; when opening, 52B background with 50A star; when fully open, background color 52C with 50A star, fading to 50D background with 52A star; under side 50B. (3) Number of petals: Five. (4) Size of flower: 5.5 cm both in length and width.

G. *Reproductive organs.*—(1) Stamens: Five (5) in number. (a) Anther: Oblong in shape, color 11D. (b) Pollen color: 10D. (2) Pistils: (a) Stigma: Round in shape; color, 66A. (b) Style: 137A. (c) Ovary: Superior, 5-celled, 1.25 cm in length and 137C in color.

H. *Spur.*—An approximately 5.75 cm long spur originates from base of major sepal, and is curved at the end; spur color is approximately 148C.

Disease reistance: No fungal or bacterial problems observed to date.

Seed development: The new cultivar very rarely forms seed pods.

CHART A

| Characteristic | Celebration Cherry Star | Vulcain | Sundazzle |
|---|---|---|---|
| Plant height | 10 ± 1 cm | 11 ± 1 cm | 8 ± 1 cm |
| Plant diameter | 32 ± 2 cm by 26 ± 3 cm | 30 ± 3 cm by 26 ± 2 cm | 27 ± 2 cm by 23 ± 1 cm |
| Branches/plant | 5 ± 1 | 5 ± 1 | 5 ± 1 |
| Foliage color mature leaves (top side) | 147a | 147a | 147a |
| Foliage color young leaves (top side) | 147a | 147a | 146a |
| Foliage color (bottom) | 59a | 59a | 59a |
| Flower color background (top side) | 52c | 56c | 49d |
| Flower color star (top side) | 50a | 50a | 50a |
| Flower color (bottom) | 50b | 50a | 50b |
| Flower size | 5.5 × 5.5 cm | 5.5 × 4.5 cm | 5.0 × 5.0 cm |

I claim:

1. A new and distinct Impatiens plant named Celebration Cherry Star, as illustrated and described.

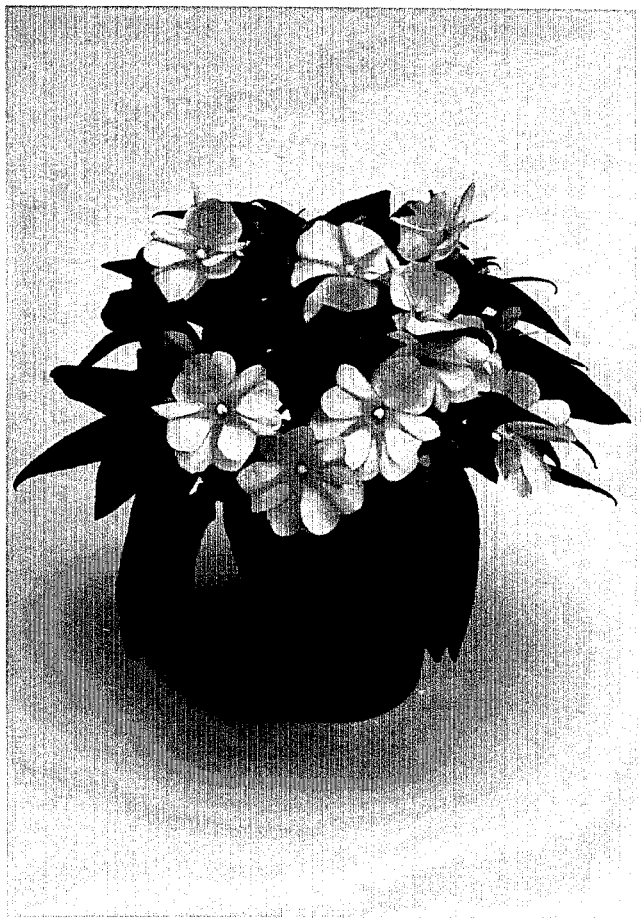
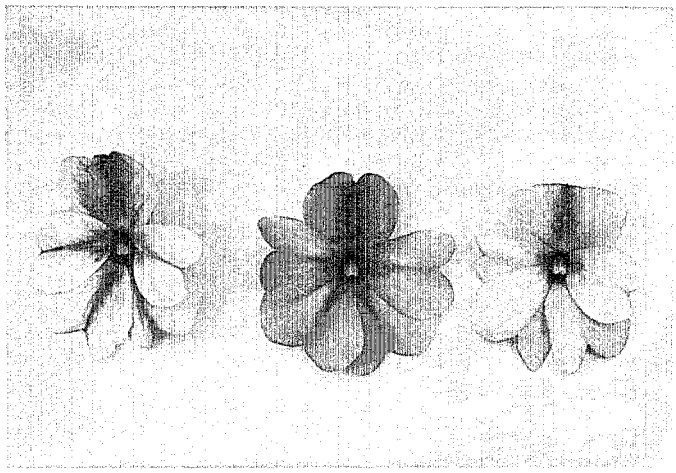

* * * * *